US010345308B2

(12) United States Patent
Wang

(10) Patent No.: US 10,345,308 B2
(45) Date of Patent: Jul. 9, 2019

(54) HUMAN SERUM BIOMARKERS OF PROSTATE CANCER AND SARS-COV

(71) Applicant: SRI INTERNATIONAL, Menlo Park, CA (US)

(72) Inventor: Denong Wang, Menlo Park, CA (US)

(73) Assignee: SRI INTERNATIONAL, Menlo Park, CA (US)

(*) Notice: Subject to any disclaimer, the term of this patent is extended or adjusted under 35 U.S.C. 154(b) by 174 days.

(21) Appl. No.: 14/521,787

(22) Filed: Oct. 23, 2014

(65) Prior Publication Data
US 2015/0051106 A1 Feb. 19, 2015

Related U.S. Application Data

(63) Continuation of application No. PCT/US2013/037933, filed on Apr. 24, 2013.

(60) Provisional application No. 61/637,674, filed on Apr. 24, 2012, provisional application No. 61/759,745, filed on Feb. 1, 2013.

(51) Int. Cl.
*G01N 33/574* (2006.01)
*G01N 33/53* (2006.01)

(52) U.S. Cl.
CPC ....... *G01N 33/57434* (2013.01); *G01N 33/53* (2013.01)

(58) Field of Classification Search
None
See application file for complete search history.

(56) References Cited

U.S. PATENT DOCUMENTS

| 5,902,725 | A | 5/1999 | Robbins et al. | |
|---|---|---|---|---|
| 6,596,476 | B1* | 7/2003 | Lesniewski | C07K 14/005 435/5 |
| 7,981,625 | B2 | 7/2011 | Wang et al. | |
| 2003/0109420 | A1* | 6/2003 | Valkirs | G01N 33/53 435/7.1 |
| 2006/0188951 | A1* | 8/2006 | Mook | G01N 33/6854 435/7.92 |
| 2006/0269971 | A1* | 11/2006 | Diamandis | G06Q 50/22 435/7.23 |
| 2008/0305476 | A1* | 12/2008 | Robertson | G01N 33/564 435/6.11 |
| 2009/0258792 | A1* | 10/2009 | Wang | C07K 16/3069 506/9 |
| 2010/0178292 | A1 | 7/2010 | Wang et al. | |
| 2011/0177090 | A1 | 7/2011 | Wang et al. | |

FOREIGN PATENT DOCUMENTS

| CN | 104428674 A | 3/2015 |
|---|---|---|
| WO | WO 2006/102687 A1 | 9/2006 |
| WO | WO 2013/163269 A1 | 10/2013 |

OTHER PUBLICATIONS

Lai-Xi et al., Chemistry & Biology, vol. 11, pp. 127-134, published Jan. 2004.*
Zhou et al., "Carbohydrate Cluster Microarrays Fabricated on Three-Dimensional Dendrimeric Plateforms for Functional GLycomics Exploration", Journal of Proteome Research, vol. 8, pp. 5031-5040, published Sep. 30, 2009.*
Faghihnejad et al., "Hydrophobic interactions between polymer surfaces: using polystyrene as a model system", Soft Matter, vol. 8, pp. 2746-2759, published Jan. 27, 2012.*
Ruobing et al., "A Practical Protocol for Carbohydrate Microarrays", Chemical Genomics, vol. 310, pp. 241-252, published 2005.*
Abel Pd, et al. "Assessment of serum CA 19.9 as a tumour marker in patients with carcinoma of the bladder and prostate". Br J Urol. 1987; 59(5):427-9.
Abel PD, et al. "Detection of blood group antigens in frozen sections of prostatic epithelium". Br J Urol.1987;59(5):430-5.
Blixt O, et al. "Autoantibodies to aberrantly glycosylated MUC1 in early stage breast cancer are associated with a better prognosis". Breast Cancer Res. 2011;13(2):R25.
Chandrasekaran EV, et al. "Analysis of the specificity of sialyltransferases toward mucin core 2, globo, and related structures. Identification of the sialylation sequence and the effects of sulfate, fucose, methyl, and fluoro substituents of the carbohydrate chain in the biosynthesis of selectin and siglec ligands, and novel sialylation by cloned alpha2,3(0)sialyltransferase". Biochemistry. 2005; 44(47):15619-35.
Ghazizadeh M, et al. ""Immunohistochemical localization of T antigen-like substance in benign hyperplasia and adenocarcinoma of the prostate"". J Urol. 1984;132(6):1127-30.
Handerson T, et al. "Beta1,6-branched oligosaccharides and coarse vesicles: a common, pervasive phenotype in melanoma and other human cancers". Cancer Res. 2003; 63(17):5363-9.
Jorgensen T, et al., "Up-regulation of the oligosaccharide sialyl LewisX: a new prognostic parameter in metastatic prostate cancer". Cancer Res. 1995; 55(9):1817-9.
Lange T, et al. "Human Prostate Cancer in a Clinically Relevant Xenograft Mouse Model: Identification of beta(1,6)-branched Oligosaccharides as a Marker of Tumor Progression". Clin Cancer Res.; 2012.
Lau KS, et al."N-Glycans in cancer progression".Glycobiology. 2008; 18(10):750-60.
Li H, "Design and synthesis of a template-assembled oligomannose cluster as an epitope mimic for human HIV-neutralizing antibody 2G12". Org Biomol Chem. 2004; 2(4):483-8.
Liu Y, et al. "Neoglycolipid-based oligosaccharide microarray system: preparation of NGLs and their noncovalent immobilization on nitrocellulose-coated glass slides for microarray analyses". Methods Mol Biol. 2012; 808:117-36.

(Continued)

*Primary Examiner* — Tracy Vivlemore
*Assistant Examiner* — Nam P Nguyen
(74) *Attorney, Agent, or Firm* — Ballard Spahr LLP

(57) ABSTRACT

Anti-carbohydrate antibodies are detected by (a) contacting an array of oligomannose-serum albumin conjugates immobilized on a substrate with an antibody-containing serum sample under conditions wherein TM10 antibodies bind the oligomannose of the conjugates at at least micromolar affinity; and (b) detecting resultant binding of specific antibodies of the sample to the oligomannose of the conjugates, as indicative of the anti-carbohydrate antibodies.

8 Claims, No Drawings

(56) References Cited

OTHER PUBLICATIONS

Moriyama H, et al. "T antigen expression in benign hyperplasia and adenocarcinoma of the prostate". Urol Int. 1987; 42(2):120-3.
Newsom-Davis TE, et al. "Enhanced immune recognition of cryptic glycan markers in human tumors". Cancer Res. 2009; 69(5):2018-25.
Ni J, et al. "Toward a carbohydrate- based HIV-1 vaccine: synthesis and immunological studies of oligomannose-containing glycoconjugates". Bioconjug Chem. 2006;17(2):493-500.
Ohyama C, et al. "Carbohydrate structure and differential binding of prostate specific antigen to Maackia amurensis lectin between prostate cancer and benign prostate hypertrophy". Glycobiology. 2004; 14(8):671-9.
Padler-Karavani V, et al. "Human xeno-autoantibodies against a non-human sialic acid serve as novel serum boimarkers and immunotherapeutics in cancer". Cancer Res,2011; 71(9): 3352-63.
Palma As, et al. "The human epithelial carcinoma antigen recognized by monoclonal antibody AE3 is expressed on a sulfoglycolipid in addition to neoplastic mucins". Biochem Biophys Res Commun. 2011; 408(4):548-52.
Prakash S, et al. ""Glycotyping of prostate specific antigen"", Glycobiology. 2000; 10(2):173-6.
Sanders RW, et al. "The mannose-dependent epitope for neutralizing antibody 2G12 on humanimmunodeficiency virus type 1 glycoprotein gp120". J Virol. 2002; 76(14):7293-305.
Satoh M, et al. "Glycolipid expression in prostatic tissue and analysis of the antigen recognized by antiprostatic monoclonal antibody APG1". Urol Int. 1992 ;48(1):20-4.
Scanlan CN, et al. "The broadly neutralizing anti-human immunodeficiency virus type 1 antibody 2G12 recognizes a cluster of α1-->2 mannose residues on the outer face of gp120". J Virol. 2002; 76(14):7306-21.
Seidl KJ, et al. "Frequent occurrence of identical heavy and light chain Ig rearrangements". Int Immunol. 1997; 9(5):689-702.
Seidl KJ, et al. "Recurrent identical rearrangement and repeated expression of identical heavy and light chains in single antiphosphatidylcholine B cells". Ann NY Acad Sci. 1997;815:484-8.
Smith K, et al. "Rapid generation of fully human monoclonal antibodies specific to a vaccinating antigen". Nat Protoc. 2009; 4(3):372-84.
Tabares et al., "Different glycan structures in prostate-specific antigen from prostate cancer sera in relation to seminal plasma PSA", Glycobiology, vol. 16, No. 2, pp. 132-145 (2006).
Trkola A, et al. "Human monoclonal antibody 2G12 defines a distinctive neutralization epitope on the gp120 glycoprotein of human immunodeficiency virus type 1". J Virol., 1996; 70(2):1100-8.
Wandall HH, et al. "Cancer biomarkers defined by autoantibody signatures to aberrant 0- glycopeptide epitopes". Cancer Res. 2010; 70(4):1306-13.
Wang D, et al. "Antibodies, Specificity. In: Encyclopedia of Immunology", Edn. Second (ed. Delves & Roitt). 1998:148-54.
Wang D, et al. "Carbohydrate microarrays for the recognition of cross-reactive molecular markers of microbes and host cells". Nat Biotechnol. 2002; 20(3):275-81.
Wang D, et al. ""Glycan arrays lead to the discovery of autoimmunogenic activity of Sars-CoV"". Physiol Genomics. 2004;18(2):245-8.
Wang D, et al. ""Prostate cancer glycan markers and auto-antibody signatures"". U.S. Pat. No. 7,981,625. Jul. 19, 2011. Assigned to the Board of Trustees of the Leland Stanford Junior University, Palo Alto, CA (US); 2011.
Wang D, et al. "Reaction of germinal centers in the T-cell-independent response to the bacterial polysaccharide alpha (1-->6)dextran". Proc Natl Acad Sci U S A. 1994; 91(7):2502-6.
Wang D, et al. "The repertoire of antibodies to a single antigenic determinant". Mol Immunol. 1991; 28(12):1387-97.
Wang D. "Carbohydrate antigen microarrays". Methods Mol Biol. 2012; 808:241-9.
Wang et al., "Anti-oligomannose antibodies as potential serum biomarkers of aggressive prostate cancer", Drug Development Research, vol. 74, Issue 2, pp. 65-80 (2013).
Wang LX, et al. "Binding of high-mannose-type oligosaccharides and synthetic oligomannose clusters to human antibody 2G12: implications for HIV-1 vaccine design". Chem Biol. 2004; 11(1):127-34.
Wang LX. "Toward oligosaccharide-and glycopeptide-based HIV vaccines". Curr Opin Drug Discov Devel. 2006; 9(2):194-206.
Zhang S, et al., "Expression of potential target antigens for immunotherapy on primary and metastatic prostate cancers". Clin Cancer Res. 1998; 4(2):295-302.
Zhou et al., "Carbohydrate cluster microarrays fabricated on three-dimensional dendrimeric platforms for functional glycomics exploration", Journal of Proteome Research, vol. 8, No. 11, pp. 5031-5040, (2009).
International Search Report and Written Opinion dated Aug. 6, 2013 by the International Searching Authority for International Application No. PCT/US2013/037933, filed Apr. 24, 2013 and published as WO 2013/163269 dated Oct. 31, 2013 (Applicant- SRI International) (11 Pages).
International Preliminary Report on Patentability dated Oct. 28, 2014 by the International Searching Authority for International Application No. PCT/US2013/037933, filed Apr. 24, 2013 and published as WO 2013/163269 dated Oct. 31, 2013 (Applicant- SRI International) (8 Pages).
First Office Action dated Jul. 27, 2015 by the SIPO for CN Application No. CN 201380033615.8, filed Apr. 24, 2013 and published as CN 104428674 dated Mar. 18, 2015 (Applicant- Stanford Res Inst Int) (Original- 4 pages // Translated- 6 Pages).
Second Office Action dated Mar. 23, 2016 by the SIPO for CN Application No. CN 201380033615.8, filed Apr. 24, 2013 and published as CN 104428674 dated Mar. 18, 2015 (Applicant- Stanford Res Inst Int) (Original- 9 pages // Translated- 15 Pages).
Third Office Action dated Jul. 14, 2016 by the SIPO for CN Application No. CN 201380033615.8, filed Apr. 24, 2013 and published as CN 104428674 dated Mar. 18, 2015 (Applicant- Stanford Res Inst Int) (Original- 8 pages // Translated- 12 Pages).
Re Examination Decision dated May 25, 2018 by the SIPO for CN Application No. CN 201380033615.8, filed Apr. 24, 2013 and published as CN 104428674 on Mar. 18, 2015 (Applicant- Stanford Res Inst Int) (Original- 11 pages // Translated- 8 Pages).

* cited by examiner

HUMAN SERUM BIOMARKERS OF PROSTATE CANCER AND SARS-COV

CROSS-REFERENCE TO RELATED APPLICATIONS

This application is a continuation PCT/U.S. Ser. No. 13/037933, filed Apr. 24, 2013 which claims priority to U.S. Ser. No. 61/637,674, filed Apr. 24, 2012, and to U.S. Ser No. 61/759,745, filed Feb. 1, 2013, the disclosures of which is incorporated herein by reference in its entirety.

This invention was made with government support under Grant No. 7U01CA128416-04 awarded by the National Institutes of Health. The government has certain rights in the invention.

INTRODUCTION

Prostate cancer (PCa) is the most common non-cutaneous malignancy in men. Based on autopsy studies, a significant number of American men in their 30's already have cancer in their prostates; this frequency rises to about 80% for men in their 70's. Despite such a high incidence of PCa, only 8% of men in the U.S. in their lifetime present with clinically significant disease that affects their quality of life [Stamey et al. 1993], and only 3% of all men in the U.S. die of PCa [Ries 1994]. No other human cancer possesses such an enormous disparity between the very high incidence of malignancy microscopically and the relatively low death rate. For example, breast cancer, the leading female malignancy, commands a 15% mortality rate within 5 years [DeSantis et al. 2011a; DeSantis et al. 2011b], while lung cancer, the third most common malignancy overall, commands an overwhelming 86% mortality rate within 5 years [Bach et al. 2004].

Such a striking disparity between the high incidence of occurrence and relatively low rate of death from PCa has prompted us to ask 1) are there mechanisms of host surveillance that substantially reduce the death rate from PCa; 2) can novel assays be established to detect the high-risk, high mortality status of PCa so that effective treatment can be given to these subjects to reduce the death rate from the disease; and 3) are there key immunological targets that are differentially expressed among aggressive cancer (aPCa) and other clinically indolent, non-aggressive cancers (iPCa)? Identification of such immunogenic elements is crucial for establishment of therapeutic and diagnostic strategies to improve current healthcare of PCa patients.

Our group has been investigating the potentially immunogenic carbohydrate moieties of PCa. Assessing patterns of lectin binding to tissue microarrays, we observed abnormal expression of a number of glycan markers in PCa[Wang et al. 2011]. These markers were the precursors, cores and internal sequences of N-glycans, such as oligomannoses, triantennary type II (Galβ1→4GlcNAc) chains (Tri-II) or multivalent type II chains (m-II) [Wang 2012]. A common immunological characteristic of these markers is that they are usually masked by other sugar moieties, and they belong to a class of glyco-epitopes that are normally "cryptic". Importantly, their tissue expression or amounts of exposure appear to differ dramatically among different Gleason grades of PCa and tumor metastases [Lange et al. 2012; Wang et al. 2011]. This is of potential clinical significance because Gleason grade is the strongest predictor of recurrence of PCa following definitive surgical or radiation therapy.

Subsequently, we found in an animal model study that a tumor cell-based vaccine elicited anti-Man9-cluster antibodies [Newsom-Davis et al. 2009]. In this case, Fas-ligand-transfected melanoma cells were used for animal immunization. A monoclonal antibody (mAb) TM10 established by this immunization strategy illustrates a unique binding profile in flow cytometry analysis. TM10 does not bind to the cell surface of untransformed normal cells but strongly binds a number of murine and human tumor cell lines, including those from melanoma, prostate, breast and ovarian cancers. Interestingly, our carbohydrate microarray analysis revealed that TM10 recognizes the oligomannosyl epitopes presented by (Man9)n-Keyhole limpet hemocyanin (KLH) and [(Man9)4]n-KLH [Newsom-Davis et al. 2009]. These glycoconjugates were initially constructed to display an HIV-1 neutralization epitope recognized by mAb 2G12 [Ni et al. 2006] but were found in this study to present the tumor-associated TM10-antigens.

Using carbohydrate microarrays, we further examined whether human immune systems also recognize these tumor carbohydrates and mount antibody responses. We analyzed a panel of sera from men with PCa (N=17) compared to sera from men with benign prostatic hyperplasia (BPH) (N=12). The two TM10-positive Man9-conjugates were found to be highly effective in capturing human serum IgG antibodies from both of these groups. However, the levels of antibodies captured in the cancer group were significantly higher than those detected in the BPH group [Wang 2012].

Taken together, these findings indicate that the tumor-associated TM10 antigens are immunogenic in vivo. Abnormal expression or exposure of these targets can trigger specific autoantibody responses in cancer subjects. We extended our investigation to a larger scale serological study using the Stanford cohort of radical prostatectomy specimens and sera. As summarized below, we established an ELISA to enable highly specific detection of anti-Man9-cluster antibodies, including $IgG^{Man9}$ and $IgM^{Man9}$, in human sera. We also confirmed that anti-Man9-cluster antibodies are widely present in human circulation, and that the levels of these autoantibodies significantly increase in men whose cancers contain a large volume of Gleason grades 4 and/or 5.

Relevant Art:

Aspects of this invention were published as Wang et al. 2012, J Proteomics & Bioinformatics (5:090-095, DOI: 10.4172/jpb.1000218) and Wang et al. 2013, Drug Development Research [74(2):65-80, DOI: 10.1002/ddr.21063]. U.S. Pat. No. 7,981,625.

SUMMARY OF THE INVENTION

The invention provides materials, systems and methods for detecting anti-carbohydrate antibodies. In one aspect the method comprising steps: (a) contacting an array of oligomannose-serum albumin conjugates immobilized on a substrate with an antibody-containing serum sample under conditions wherein TM10 antibodies bind the oligomannose of the conjugates at at least micromolar affinity; and (b) detecting resultant binding of specific antibodies of the sample to the oligomannose of the conjugates, as indicative of the anti-carbohydrate antibodies. In another aspect the compositions are microarrays, microwell plates or related substrates comprising an array of ordered, immobilized oligomannose-serum albumin conjugates, wherein the oligomannose of the conjugates bind TM10 antibodies at at least micromolar affinity.

In another aspect the invention provides a method for synergistically predicting the clinical outcome of a prostate hyperplasia, particularly prostate cancer, by detecting anti-carbohydrate antibodies like $IgG^{Man9}$ and PSA, the method comprising steps: (a) contacting oligomannose and prostate specific antigen (PSA) antigens with antibodies of a patient sample under conditions wherein the antibodies specifically bind the antigens; and (b) detecting resultant specific binding of the antibodies to the antigens, wherein the specific binding of the antibodies is synergistic in predicting the clinical outcome of a prostate hyperplasia.

The invention includes particular embodiments, and all combinations thereof wherein:

the serum albumin is HSA or BSA;
the oligomannose is man5 or man9;
the conjugate has the structure (Man9GlcNAc2Asn)n-BSA or (Man5GlcNAc2Asn)n-BSA;
the array comprises man5- and man9-serum albumin conjugates immobilized at distinct positions on the substrate;
the array further comprises ASOR, AGOR and/or OR immobilized at distinct positions on the substrate;
the method selectively detects TM10-like anti-Man9 cluster from an unselected repertoire of human serum antibodies;
the sample is from a person with prostate dysplasia and the amount of the resultant binding indicates status of the prostate hyperplasia, such as wherein the prostate dysplasia is aggressive prostate cancer.
the substrate is an epoxy-coated glass slide and the array is a microarray;
the substrate is a hydrophobic polystyrene surface coated plastic microplate (e.g. NUNC Polysorp);
the conjugates are immobilized by coating the surface (e.g. polystyrene microplate) with Man9-BSA at 20 ug/ml in 0.1 M Sodium Bicarbonate Buffer Solution, pH 9.6 and incubating at 37C. for 2 hrs; and/or
the contacting step comprises coating the conjugates with the serum sample at a dilution of 1:500 in 1% BSA, PBST and incubating at 4C. for 8-12 hrs.

For example, in one combination of particular embodiments: the substrate is a hydrophobic polystyrene surface coated plastic microplate; the conjugates are immobilized by coating the surface with Man9-BSA at 20 ug/ml in 0.1 M Sodium Bicarbonate Buffer Solution, pH 9.6 and incubating at 37C for 2 hrs; and the contacting step comprises coating the conjugates with the serum sample at a dilution of 1:500 in 1% BSA, PBST and incubating at 4C. for 8-12 hrs.

The invention specifically provides all combinations of the recited aspects, as if each had been laboriously individually set forth.

DETAILED DESCRIPTION OF PARTICULAR EMBODIMENTS

The invention provides selective detection of TM10-like anti-Man9 cluster from a large repertoire of human serum antibodies with significantly improved, over prior art methods, ratio of signal/background for detecting anti-carbohydrate antibodies in human serum. Inventive aspects include: 1) ASOR, AGOR and OR panel for detection of autoantibodies in prostate cancer; 2) Man9-BSA, e.g. (Man9GlcNAc2Asn)n-BSA, and Man5-BSA panel probes for detection of aggressive PCa; 3) microarray arrays for detection of TM10 and TM10-like antibodies; and 4) ELISA protocols for detection of TM10-like human serum autoantibodies in normal, BPH and PCa, and especially for aggressive PCa.

Unless otherwise indicated, the disclosure is not limited to specific procedures, materials, or the like, as such may vary.

The terminology used herein is for the purpose of describing particular embodiments only and is not intended to be limiting. The singular forms "a," "an," and "the" include plural referents unless the context clearly dictates otherwise.

The invention encompasses all combinations of recited particular and preferred embodiments. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

Example 1

Anti-oligomannose Antibodies as Potential Serum Biomarkers of Aggressive Prostate Cancer This study bridges a carbohydrate microarray discovery and a large-scale serological validation of anti-oligomannose antibodies as novel serum biomarkers of aggressive prostate cancer (PCa). Experimentally, a Man9-cluster-specific ELISA was established to enable sensitive detection of anti-Man9 antibodies in human sera. A large-cohort of men with PCa or benign prostatic hyperplasia (BPH) whose sera were banked at Stanford University was characterized using this assay. Subjects included patients with 100% Gleason grade 3 cancer (N=84), with Gleason grades 4 and/or 5 cancer (N=204), and BPH controls (N=135). Radical prostatectomy Gleason grades and biochemical (PSA) recurrence served as key parameters for serum biomarker evaluation. It was found that $IgG^{Man9}$ and $IgM^{Man9}$ were widely present in the sera of men with BPH, as well as those with cancer. However, these antibody reactivities were significantly increased in the subjects with the largest volumes of high grade cancer. Detection of serum $IgG^{Man9}$ and $IgM^{Man9}$ significantly predicted the clinical outcome of PCa post-radical prostatectomy. Given these results, we disclose that $IgG^{Man9}$ and $IgM^{Man9}$ are novel serum biomarkers for monitoring aggressive progression of PCa, and oligomannosyl antigens use useful targets for PCa sub-typing and targeted immunotherapy.

Materials and Methods

The Stanford cohort of radical prostatectomy specimens and sera. This cohort included men whose cancers were known to be composed entirely of Gleason grade 3 (Gr3) (N=84), men whose cancers contained 1.0-100% Gleason grades 4 and/or 5 (Gr4/5) cancer (N=204), and the BPH controls who were biopsy-confirmed to be negative for PCa (N=135). The BPH cohort was selected from men who had undergone two rounds of systematic prostate biopsies to rule out the presence of cancer. The cancer cohort was selected from men who had undergone radical prostatectomy at Stanford and whose prostates were sectioned at 3-mm step-intervals and quantitatively characterized for eight morphological variables [Stamey et al. 1993; Stamey et al. 1999]. Mean age was 67.3 (47-88), 61.35 (37-75) and 63.73 (41-80) years for BPH, Gr3 and Gr4/5, respectively. Mean of follow-up days was 2437.63 (221-4884) for Gr3 and 2374.27 (292-6174) for Gr4/5 with failure defined as biochemical (PSA) recurrence.

Specimens used were banked at Stanford University between 1984 and 2006. Blood was obtained during the pre-operative consultation prior to radical prostatectomy and collected in tubes with silica clot activator. Following centrifugation, the sera were collected and stored at −80° C. as aliquots until analysis. Sera from men with BPH were obtained during office visits to the Stanford Department of Urology for symptoms of BPH. All were biopsied at least twice and confirmed to be negative for cancer.

Carbohydrate antibodies and antigens. MAb TM10 [Newsom-Davis et al. 2009] was kindly provided by Dr. Thomas E Newsom-Davis and mAb 2G12 by the NIH AIDS Research and Reference Reagent Program. A biotinylated anti-human IgM antibody, an alkaline phosphatase (AP)-conjugated anti-human IgG, and a horseradish peroxidase (HRP)-streptavidin conjugate were purchased from Sigma-Aldrich (St. Louis, Mo.). Biotinylated Concanavalin A (Con A) was purchased from EY Laboratories, Inc. (San Mateo, Calif.).

TABLE 1

Carbohydrate antigens and control reagents

| Probes | Description | References |
|---|---|---|
| Spotting markers | Streptavidin-Cy3, -Cy5 and - FITC | Here |
| Man5-BSA | (Man5GlcNAc2Asn)n-BSA | Here |
| Man9-BSA | (Man9GlcNAc2Asn)n-BSA | Here |
| Man9Gn2Asn | Man9GlcNAc2Asn | Wang LX et al, *Chem. Biol.*, 11(1): 127 (2004) |
| Man9-KLH | (Man9GlcNAc2Asn)n-KLH | Ni et al, BioconjugateChem., 17(2): 493 (2006) |
| M9(2G12)-KLH | [(Man9GlcNAc2Asn)4]n-KLH, mAb 2G12 positive | Ni et al, BioconjugateChem., 17(2): 493 (2006) |
| P-Man(Y2448) | Phosphomannan, Pichia (Hansenula) holstii NRRL B-2448 | Kabat et al., J. Exp. Med. 164, 642 (1986) |
| IM3-BSA | Isomaltotriose-BSA | Zopf et al., Methods Enzymol. 50, 163 (1978) |
| IM6-BSA | Isomaltohexaose-BSA | Zopf et al., Methods Enzymol. 50, 163 (1978) |

Synthesis and characterization of oligomannosyl conjugates. $Man_9GlcNAc_2Asn$ and $Man_5GlcNAc_2Asn$ were prepared following the reported method [Wang et al. 2004]. (Man9)n-KLH and [(Man9)4]n-KLH were prepared as previously described [Ni et al. 2006]. The synthesis of the glycoconjugates, (Man5)n-BSA and (Man9)n-BSA, is described in the following procedures:

High-performance liquid chromatography (HPLC). Analytical RP-HPLC was performed on a Waters 626 HPLC instrument with a Symmetry300™ $C_{18}$ column (5.0 um, 4.6×250 mm) at 40° C. The Symmetry300 column was eluted with water containing 0.1% TFA within 10 min at a flow rate of 1 mL/min (Method A). Preparative HPLC was performed on a Waters 600 HPLC instrument with a preparative Symmetry300™ $C_{18}$ column (7.0 m, 19×250 mm) These columns were eluted with water containing 0.1% TFA at a flow rate of 12 mL/min Mass spectrometry (MS). The ESI-MS Spectra were measured on a Waters Micromass ZQ-4000 single quadruple mass spectrometer.

$Man_9GlcNAc_2Asn$-Maleimide. A solution of $Man_9GlcNAc_2Asn$ (20 mg) and N-(beta-Maleimidopropyloxy) succinimide ester (BMPS) (26 mg) in a phosphate buffer (50 mM, 3 mL, pH 7.4) containing 20% acetonitrile was stirred at 23° C. for 3 hours. The residue was subject to the preparative HPLC purification to give the product $Man_9GlcNAc_2Asn$-maleimide (20 mg, 93%). Analytical HPLC (method A): $t_R$=5.7 min; ESI-MS: calculated M=2149; found 1076.1 $[M+2\ H]^{2+}$.

$Man_5GlcNAc_2Asn$-Maleimide. A solution of $Man_5GlcNAc_2Asn$ (3 mg) and BMPS (6 mg) in a phosphate buffer (50 mM, 0.35 mL, pH 7.4) containing 20% acetonitrile was stirred at 23° C. for 3 hours. The residue was subject to the preparative HPLC purification to give the product $Man_5GlcNAc_2Asn$-maleimide (2.6 mg, 78%). Analytical HPLC (method A): $t_R$=5.5 min; ESI-MS: calculated M=1501; found 751.2 $[M+2\ H]^{2+}$.

BSA-SH. A mixture of BSA (40 mg) and 2-iminothiolane (20 mg) in a phosphate buffer (50 mM, 2 mL, pH 7.2, containing 5 mM EDTA) was shaken at 23° C. for 2 hours. The residue was subject to size-exclusion chromatography on a Sephadex G-25 column. The column was eluted with a phosphate buffer (20 mM, pH 7.2). The protein fractions were combined and quantified by Bradford protein assay (for protein quantity) and free sulfhydryl assay using Ellman's reagent (for free thiol quantity). The resultant BSA-SH was 41 mg containing 32.6 µM free thiol groups.

(Man9)n-BSA. A solution of BSA-SH (41 mg, containing 32.6 µM free thiols) and $Man_9GlcNAc_2Asn$-maleimide (10 mg) in a phosphate buffer (20 mM, 10 mL, pH 7.2, containing 5 mM EDTA) was shaken at 23° C. for 3 hours. The solution was lyophilized and the residue was subject to size-exclusion chromatography on a Sephadex G-25 column The column was eluted with phosphate buffer (10 mM, pH 6.6). The protein fractions were combined to give the $Man_9GlcNAc_2$-BSA (40 mg). The carbohydrate component was quantified by anthrone assay (6.1 mg carbohydrates, 15% w/w in total $Man_9GlcNAc_2$-BSA).

(Man5)n-BSA. A solution of BSA-SH (6 mg, containing 4.8 µM free thiols) and $Man_5GlcNAc_2Asn$-maleimide (2.5 mg) in phosphate buffer (20 mM, 1.5 mL, pH 7.2, containing 5 mM EDTA) was shaken at 23° C. for 3 hours. The residue was subjected to size-exclusion chromatography on a Sephadex G-15 column. The column was eluted with phosphate buffer (10 mM, pH 6.6). The protein fractions were combined to give the $Man_5GlcNAc_2$-BSA (6 mg). The carbohydrate component was quantified by anthrone assay (1.15 mg carbohydrates, 19% w/w in total $Man_5GlcNAc_2$-BSA).

Carbohydrate microarrays. Carbohydrate antigens of various complexities were dissolved in PBS (glyco-protein conjugates) or saline (polysaccharides), and spotted onto SuperEpoxy 2 Protein slides (ArrayIt Corporation, Sunnyvale, Calif.) by a high-precision robot designed to produce cDNA microarrays (Cartesian Technologies' PIXSYS 5500C). Immediately before use, the printed microarray slides were washed in 1XPBS at RT for 5 minutes, and blocked with 1%BSA-PBS at RT for 30 minutes. They were then incubated with 50 ul of antibodies or lectins at RT for 1 hour followed by washing and then incubated with titrated secondary antibodies or streptavidin conjugates with distinct fluorescent tags, Cy5, PE, or FITC, at RT for 30 minutes. The stained slides were rinsed five times and spin-dried at room temperature before scanning for fluorescent signals. The ScanArray5000A Microarray Scanner (PerkinElmer Life Science) was used to scan the stained microarrays. Fluorescent intensity values for each array spot and its background were calculated using ScanArray Express software (PerkinElmer Life Science).

Antigen-specific ELISA Assays. A protocol described previously [Wang et al. 2002] for detection of anti-carbohydrate antibodies was followed with modifications. In brief, (Man9)n-BSA or (Man5)n-BSA was diluted in 0.1 M Sodium Bicarbonate Buffer Solution, pH 9.6, for coating on ELISA microplates followed by blocking using 1% BSA, PBST. Human serum was diluted at 1:500 in 1% BSA, PBST for ELISA. The bound anti-Man9-cluster antibodies were revealed by a combination of conjugated secondary antibodies, including an alkaline phosphatase (AP)-conjugate of goat anti-human IgG-Fc-specific antibody and a biotinylated goat anti-human IgM-Fc-specific antibody followed by horseradish peroxidase (HRP)-streptavidin-conjugate.

Statistical analyses. SAS Institute's JMP and JMP-Genomics software (Cary, N.C.) were applied in the following analyses:

Carbohydrate microarrays: Microarray datasets collected by ScanArray Express were further analyzed using JMP-Genomics.

ELISA: Oneway ANOVA was performed to compare the ELISA results obtained among groups and/or subgroups. A nonparametric statistical test (Wilcoxon rank-sum method) was applied to calculate the significance of differences among comparative groups. Least Squares Fit analysis in Fit Model mode was applied to estimate the weight of a serum marker or a combination of markers in predicting the percentage or volume of Gr4/5 cancer. Nominal Logistic Fit model was applied to investigate the performance of a serum marker as a classifier for differential diagnosis of PCa or prognosis of clinical outcome of the disease. REML (restricted maximum likelihood) method was applied in Associations and Multivariate analyses to estimate the performance of serum markers in combination.

Results

Design and construction of a TM10-tumor antigen. The two neoglycoconjugates that we applied in previous microarray studies, (Man9)n-KLH and [(Man9)4]n-KLH, were constructed to study immune responses to HIV-1 carbohydrates [Newsom-Davis et al. 2009; Ni et al. 2006; Wang et al. 2011]. We reasoned that in an immunoassay, the KLH carrier would have the disadvantage of capturing irrelevant anti-KLH antibodies if such specificities were present in human sera. We therefore constructed an additional neoglycoconjugate, (Man9)n-BSA, to selectively detect anti-Man9-cluster antibodies.

To determine whether (Man9)n-BSA preserved the tumor-specific TM10-glyco-epitopes, we characterized this compound in a carbohydrate microarray analysis. (Man9)n-BSA is similar to (Man9)n-KLH in the linkage used for coupling oligomannoses to a protein carrier and in the molar ratio between the Man9 unit and corresponding carrier. By contrast, [(Man9)4]n-KLH was constructed by introducing a defined scaffold to display the tetra-valent oligomannose clusters in order to mimic the high-density Man9-clusters expressed by the gp120 glycoprotein of HIV-1 [Li and Wang 2004; Ni et al. 2006]. Its expression of the HIV-1-specific glyco-epitopes is determined by binding to an HIV-1 neutralization mAb 2G12 [Sanders et al. 2002; Scanlan et al. 2002; Trkola et al. 1996; Wang and Herzenberg 2011].

As we expected, the three Man9-cluster conjugates are similarly reactive with Con A but are differentially reactive with 2G12. Con A detects terminal mannoses with the C-3, C-4, and C-5 hydroxyl groups [Goldstein et al. 1965]. Its binding to these conjugates is, thus, independent of the Man9-cluster configurations. [(Man9)4]n-KLH is highly and selectively bound by 2G12, which reflects its expression of the HIV-1-specific M9(2G12) glyco-epitopes. Differing from [(Man9)4]n-KLH, (Man9)n-BSA and (Man9)n-KLH are highly reactive with anti-tumor mAb TM10. Thus, this microarray analysis demonstrates that the newly designed glyco-conjugate, (Man9)n-BSA, preserves well the TM10-reacting epitopes. Given that (Man9)n-BSA and (Man9)n-KLH differ in the protein carrier, the TM10-glyco-epitopes are clearly presented by their common Man9-cluster components. Since the two TM10-positive conjugates are only marginally reactive with 2G12, the tumor-associated TM10-epitopes differs from the HIV-1-specific 2G12-glycoepitopes.

Establishment of a highly specific ELISA for detection of TM10-like antibodies. We further examined whether (Man9)n-BSA is suitable for an ELISA platform to support specific detection of TM10-like anti-Man9-cluster antibodies. For this investigation, we constructed an additional glyco-conjugate, (ManS)n-BSA. (Man9)n-BSA and (ManS)n-BSA share the Man5GlcNAc2Asn-moiety and the linkage used to couple them to the BSA molecule. Differing from Man9, which displays Man$\alpha$1,2Man-moieties in the non-reducing ends, ManS expresses no terminal Man$\alpha$1,2Man-moiety but presents Man$\alpha$1,3Man and Man$\alpha$1,6Man moieties at its terminals.

We determined ELISA-binding curves of Con A and TM10, respectively, on microtiter plates coated with (Man9)n-BSA and (ManS)n-BSA. The plates were coated with a series of dilutions of the glyco-conjugates and reacted with a constant concentration of TM10 or Con A. Such an assay design is practical for epitope-mapping and measurement of the relative binding affinity of carbohydrate-anti-carbohydrate interactions. In this analysis, Con A was used to monitor whether the two glyco-conjugates were quantitatively immobilized on the ELISA plates and whether their oligomannosyl moieties were accessible for specific binding. Our results showed that Con A-binding curves with (Man9)n-BSA and (Man5)n-BSA are near linear in the ranges of antigen concentrations from 0.25-10.00 ug/ml. Both conjugates appear to be stably immobilized on ELISA plates with their terminal mannoses readily reactive with Con A. Our data also showed that TM10 is highly and selectively reactive with (Man9)n-BSA but has no binding to (Man5)n-BSA. Its Man9-binding curve is near linear in the range of antigen concentrations from 1.0-20.00 ug/ml. Thus, although both conjugates display Con A-epitopes, (Man9)n-BSA better preserves the tumor-specific TM10-glyco-epitopes.

Subsequently, we investigated the ELISA conditions for measuring anti-Man9-antibodies in human serum. We determined ELISA results with 436 sera measured at a constant dilution of 1:500 in 1% BSA PB ST. This condition was determined in preliminary experiments to maximize the ratio of anti-Man9 signal ($Ig^{Man9}$) to the assay background ($Ig^{Bg}$). ANOVA analysis shows that this assay detected highly significant levels of IgG$^{Man9}$ (P<0.0001) and IgM$^{Man9}$ (P<0.0001) above background. Receiver operating characteristic (ROC) plots produced area under the curve (AUC) values of 0.99709 and 0.97324 for detection of IgG$^{Man9}$ and IgM$^{Man9}$, respectively. Thus, this assay reached the sensitivity and specificity required to single out anti-Man9-cluster antibodies from the repertoire of human serum antibodies.

Prostatectomy Gr4/5 cancer as "gold standard" for serum biomarker evaluation. Our next goal was to use this ELISA to measure anti-Man9-cluster antibodies in pre-prostatectomy sera obtained from men who underwent surgery at Stanford University between 1984 and 2006 to treat PCa, and men seen in the Stanford Urology Clinic during the same period with symptoms of BPH. The latter men underwent at least two rounds of ultrasound-guided needle biopsies to rule out the presence of PCa. The former were chosen from men whose prostates had been subjected to a comprehensive histopathological review by a single pathologist [Stamey et al. 1999]. The radical prostatectomy specimens were sectioned at 3-mm step intervals and 8 morphological variables were quantified. After correlating these morphologic variables with clinical data, Stamey and his colleagues [Stamey et al. 1999] recognized that the percent of Gr4/5 cancer in the tumor is the most significant prognostic marker predicting risk of biochemical failure (defined as serum PSA ≥0.07 ng/ml by the TOSOH assay on two consecutive measurements). Accordingly, we performed Nominal Logistic Fit analysis to examine whether the cohort selected for this study also illustrates such a correlation. We found that total volume of Gr4/5 and % Gr4/5 as independent classifiers for this modeling analysis produced AUC values of 0.91165 and 0.91921 for predicting biochemical recurrence, respectively. Thus, the two parameters are equally effective in predicting failure or cure after prostatectomy in this cohort. This cohort is, therefore, highly valuable for evaluating serum biomarkers of aPCa and prediction of the clinical outcome after radical prostatectomy to treat PCa.

Detection of TM10-like anti-Man9-cluster autoantibodies in men with BPH or PCa. Using the Man9-cluster ELISA to analyze the Stanford cohort, we investigated whether TM10-like antibodies are present in human circulation and whether the titers of these anti-tumor carbohydrate antibodies differ among men with BPH, men with cancer containing only Gr3, and men whose cancers contain different amounts of Gr4/5. In one experiment we analyzed 423 subjects in this cohort. These included patients with Gr3 cancer (N=84), Gr4/5 cancer (N=204), and the age-matched BPH controls (N=135). In order to examine whether detection of anti-Man9 antibodies predicted the presence of aggressive PCa, men with Gr4/5 cancers were sub-grouped into quartiles according to the volume of Gr4/5 cancer in a given subject.

IgM$^{Man9}$ was detected in all sub-groups. As determined by the Wilcoxon nonparametric test, levels of IgM$^{Man9}$ were not significantly different between men with BPH versus men with Gr3 cancer. However, the levels of IgM$^{Man9}$ in certain of the subgroups of men with Gr4/5 cancer differed significantly from the BPH and Gr3 groups. Notably, the two subgroups with the largest total volumes of Gr4/5 cancer (≥3.99 cc) expressed higher levels of IgM$^{Man9}$ than BPH (p=0.0012 and 0.0149 for BPH versus Gr4/5 3.99-7.0211 cc and BPH versus Gr4/5 7.03-40.67 cc, respectively) and Gr3 (p=0.0130 and 0.0835 for Gr3 versus Gr4/5 3.99-7.0211 cc and Gr3 versus Gr4/5 7.03-40.67 cc, respectively). Similarly to the IgM profile, we detected significant amounts of IgG$^{Man9}$ in all sub-groups. The levels of IgG$^{Man9}$ in the subgroup with the largest volume of Gr4/5 cancer (≥7.03 cc) were significantly higher than those detected in men with BPH (p=0.0084), Gr3 cancer (P=0.0064), and other subgroups of Gr4/5 cancer (P=0.0140, 0.0008 and 0.0526 for its pair with Gr4/5 <0.91 cc, Gr4/5 0.91-3.95 cc and Gr4/5 3.99-7.0211 cc, respectively).

We examined whether Ig$^{Man9}$ antibodies correlated with prostate weight, a parameter previously found to be strongly correlated to serum PSA levels [Stamey et al. 2004]. For this purpose, we sub-grouped all cancer subjects into quartiles based on the prostate weights. Neither IgM$^{Man9}$ nor IgG$^{Man9}$ levels showed correlation to the prostate weights. We also examined correlation of antibody levels with other cancer parameters, such as the volume of non-aggressive Gr3 cancer. Unlike serum PSA values, which are positively correlated to both the Gr3 volume and prostate weight, levels of serum IgM$^{man9}$ and IgG$^{man9}$ had no correlation to these parameters.

A significant portion of patients (N=259, 61.2%) in this cohort are in the PSA "grey zone", with PSA values <10.0 ng/ml. At these levels, PSA does not distinguish men with PCa from those with BPH with high specificity or predict risk of recurrence after surgery with high confidence [Stamey et al. 2004]. As shown by ANOVA analysis of these data, the performance of Ig$^{man9}$ signatures was reproduced in this challenging population. The levels of both IgM$^{man9}$ and IgG$^{man9}$ were significantly increased in the subgroups with the larger volume Gr4/5 PCa. Logistic regression analysis indicates that Ig$^{man9}$ is highly significant in predicting the clinical outcome of men post-prostatectomy. Ig$^{man9}$ plus PSA and PSA alone produced an AUC value of 0.72338 and 0.65221, respectively. This result indicates that Ig$^{man9}$ and PSA are synergistic in predicting the clinical outcome of PCa.

A scatterplot matrix was used to examine the relative values of these predictors in detection of the larger volume of Gr4/5 PCa and prediction of clinical outcome of patients. Visual inspection of the pairs of Log2-PSA, Log2-IgM$^{man9}$ and Log2-IgG$^{man9}$ reveals clusters of red dots in the upper and right sections of the plots, which are associated with increasing values of these serum markers.

Discussion

N-glycan cryptic glyco-epitopes recognized by mAb TM10 and human serum IgM$^{Man9}$ and IgG$^{Man9}$. We have demonstrated the presence of Ig$^{Man9}$ in the human circulation by a large-scale serological study of 423 subjects. This result is in striking contrast with the fact that a broad, decade-long search for induction of anti-oligomannose antibodies by HIV-1 vaccines has been unsuccessful [Barouch 2008; Ni et al. 2006; Wang 2006; Willyard 2010]. We asked, therefore, whether and how the tumor-associated oligomannosyl antigens differ from the 2G12-positive HIV-1-carbohydrates in their structural characteristics. MAb TM10 and 2G12 have served as key reagents to probe the similarities and differences between the HIV-1 carbohydrates recognized by 2G12 and the tumor-associated TM10-carbohydrates.

We characterized the binding specificities of TM10 and 2G12 by carbohydrate microarrays, which contain a panel of mannose-clusters of different structural characteristics. The two mAbs differ in binding activity with the oligomannosyl antigens of different cluster configurations. 2G12 is specific for the high-density Man9-clusters presented by [(Man9)4]n-KLH, which mimics the HIV-1 virion-presenting of the oligomannose antigens; TM10 is, however, similarly reactive with the three Man9-conjugates spotted in the same array without selectivity. In an antigen-specific ELISA, we further demonstrated that TM10 binds to (Man9)n-BSA but not to (Man5)n-BSA.(Man9)n-BSA and (Man5)n-BSA differ in their terminal mannosyl moieties. The former displays Man 1,2Man-moieties; the latter expresses no terminal Man 1,2Man-moiety but presents Man 1,3Man and Man 1,6Man moieties at its terminals. Thus, TM10 recognizes the terminal Man 1,2Man-glyco-epitopes that are also bound by 2G12. The tumor-associated TM10-antigen differs from the HIV-1-specific 2G12-antigen only by its Man9-cluster configuration.

Detection of serum Ig Man9 significantly predicts the presence of aggressive cancers. With the Stanford reference set, it is possible to examine whether a serum marker is correlated to the key surgical parameters of PCa severity, such as presence of high % and large volume Gr4/5 cancer, and whether detection of such a marker predicts the clinical outcome of the disease. To address these questions, we have performed further statistical analysis to estimate the effectiveness of IgMan9 in detection of the large volume and high % Gr4/5 cancers in PCa patients. First, we performed a Least Squares Fit analysis to test IgMMan9 and IgGMan9 for prediction of either large volume or high % Gr4/5, independently. For predicting % Gr4/5, IgMMan9 statistics are P<0.0001, RSq 0.04, and RMSE 33.614; the IgGMan9 values are P=0.0036; RSq 0.02, and RMSE 33.95. When volume of G4/5 cancer is targeted for this modeling analysis, IgMMan9 statistics are P=0.066, RSq 0.01, and RMSE 5.1788; IgGMan9 values are P=0.0008; RSq 0.03, and RMSE 5.1318. Thus, IgMMan9 and IgGMan9 significantly predict the % or volume of G4/5 cancer. The degrees of significance of each parameter, as estimated by RSq values, varied among parameters.

Next, we examined whether $IgM^{Man9}$ and $IgG^{Man9}$ improve the predictive effects in synergy with PSA, which is predictive of the cancer volume or prostate weight. We observed that PSA plus $Ig^{Man9}$ ($IgM^{Man9}$ and $IgG^{Man9}$) are highly significant in predicting the % or volume of G4/5 cancer in this cohort. For detection of % Gr4/5 cancer, the RSquare (RSq) values of PSA and PSA plus $Ig^{Man9}$ are 0.07 and 0.12, respectively. That means the two markers in combination increased the weight of influence from 7% by PSA alone to 12% of the total variation. When the volume of Gr4/5 was calculated, RSq values of PSA and PSA plus $Ig^{Man9}$ are 0.24 and 0.28, which are weighted 24% and 28%, respectively.

$Ig^{Man9}$ and PSA illustrate synergistic effects in predicting clinical outcome post-radical prostatectomy. Prostate needle biopsy (PNBx) is another principal clinical examination that is currently employed to risk stratify newly diagnosed PCa patients. In the United States, ~90% of patients are diagnosed with clinical stage T1c, which is characterized by an elevated PSA but normal digital rectal exam with a PNBx revealing malignancy. Most PCa is diagnosed in the setting of a low PSA (<10 ng/ml) and no palpable prostate mass (cT1c). In these cases, the PNBx Gleason score, i.e., sum of the two most prominent Gleason grades, is the predominant factor used to render clinical decision of either aPCa or iPCa. However, there are many cases of under- and over-grading in PNBx as compared to the radical prostatectomy Gleason scores [D'Amico et al. 1999; Grossfeld et al. 2001; Isariyawongse et al. 2008]. Given a recent report on 2963 cases of PCa receiving radical prostatectomy in Duke University [Isariyawongse et al. 2008], the rates of discrepancies between the diagnostic and the pathologic Gleason sums are substantially high. Overall, 55.8% of the diagnostic Gleason sums differed from those on final surgical pathology, including the under-graded diagnosis in 41.2% of cases and the over-graded in 12.8% of cases.

It is understood that neither serum PSA levels nor PNBx correctly reveal the volume or grade of cancer in the prostate [King et al. 2004; Noguchi et al. 2001]. Measurement of the volume or % of Gr4/5 PCa in a subject can only be achieved after radical prostatectomy. Thus, identification of $Ig^{Man9}$ as a predictor of the large volume/high percentage of Gr4/5 PCa, a class of well-defined aggressive PCa, especially in the population of low PSA (<10 ng/ml), is of high significance. Nevertheless, the sum of the prognostic power of the two serum markers as calculated herein (~72%) remains significantly lower than the ~91% accuracy as estimated by the ROC curves when surgical % or volume of Gr4/5 cancer serves as the predictor of clinical status. A better performance of PCa prognosis and differential diagnosis may be achieved by integrating the diagnostic potential of these anti-glycan antibodies and other serum markers, such as autoantibodies to PCa-specific proteins [Massoner et al. 2012], O-glycopeptides [Wandall et al. 2010] and the xeno-autoantibodies elicited by the dietary non-human sialic acid Neu5Gc [Padler-Karavani et al. 2011].

References:

Bach P B, Elkin E B, Pastorino U, Kattan M W, Mushlin A I, Begg C B, Parkin D M. 2004. Benchmarking lung cancer mortality rates in current and former smokers. Chest 126(6):1742-9.

Barouch DH. 2008. Challenges in the development of an HIV-1 vaccine. Nature 455(7213):613-9.

D'Amico A V, Renshaw A A, Arsenault L, Schultz D, Richie J P. 1999. Clinical predictors of upgrading to Gleason grade 4 or 5 disease at radical prostatectomy: potential implications for patient selection for radiation and androgen suppression therapy. Int J Radiat Oncol Biol Phys 45(4): 841-6.

DeSantis C, Howlader N, Cronin K A, Jemal A. 2011a. Breast cancer incidence rates in U.S. women are no longer declining Cancer Epidemiol Biomarkers Prev 20(5):733-9.

DeSantis C, Siegel R, Bandi P, Jemal A. 2011b. Breast cancer statistics, 2011. CA Cancer J Clin 61(6):409-18.

Goldstein I J, Hollerman C E, Smith E E. 1965. Protein-Carbohydrate Interaction. Ii. Inhibition Studies on the Interaction of Concanavalin a with Polysaccharides. Biochemistry 4:876-83.

Grossfeld G D, Chang J J, Broering J M, Li Y P, Lubeck D P, Flanders S C, Carroll P R. 2001. Under staging and under grading in a contemporary series of patients undergoing radical prostatectomy: results from the Cancer of the Prostate Strategic Urologic Research Endeavor database. J Urol 165(3):851-6.

Isariyawongse B K, Sun L, Banez L L, Robertson C, Polascik T J, Maloney K, Donatucci C, Albala D, Mouraviev V, Madden J F and others. 2008. Significant discrepancies between diagnostic and pathologic Gleason sums in prostate cancer: the predictive role of age and prostate-specific antigen. Urology 72(4):882-6.

King C R, McNeal J E, Gill H, Presti J C, Jr. 2004. Extended prostate biopsy scheme improves reliability of Gleason grading: implications for radiotherapy patients. Int J Radiat Oncol Biol Phys 59(2):386-91.

Lange T, Ullrich S, Midler I, Nentwich M F, Stuebke K, Feldhaus S, Knies C, Hellwinkel O J C, Vessella R L, Abramjuk C and others. 2012. Human Prostate Cancer in a Clinically Relevant Xenograft Mouse Model: Identification of β(1,6)-branched Oligosaccharides as a Marker of Tumor Progression. Clinical Cancer Res. Published OnlineFirst on Jan. 18, 2012; DOI:10.1158/1078-0432.CCR-11-2900.

Li H, Wang LX. 2004. Design and synthesis of a template-assembled oligomannose cluster as an epitope mimic for human HIV-neutralizing antibody 2G12. Org Biomol Chem 2(4):483-8.

Massoner P, Lueking A, Goehler H, Hopfner A, Kowald A, Kugler K G, Amersdorfer P, Horninger W, Bartsch G, Schulz-Knappe P and others. 2012. Serum-autoantibodies for discovery of prostate cancer specific biomarkers. Prostate 72(4):427-36.

Newsom-Davis T E, Wang D, Steinman L, Chen P F, Wang L X, Simon A K, Screaton G R. 2009. Enhanced immune recognition of cryptic glycan markers in human tumors. Cancer Res 69(5):2018-25.

Ni J, Song H, Wang Y, Stamatos N M, Wang L X. 2006. Toward a carbohydrate-based HIV-1 vaccine: synthesis and immunological studies of oligomannose-containing glycoconjugates. Bioconjug Chem 17(2):493-500.

Noguchi M, Stamey T A, McNeal J E, Yemoto C M. 2001. Relationship between systematic biopsies and histological features of 222 radical prostatectomy specimens: lack of prediction of tumor significance for men with nonpalpable prostate cancer. J Urol 166(1):104-9; discussion 109-10.

Padler-Karavani V, Hurtado-Ziola N, Pu M, Yu H, Huang S, Muthana S, Chokhawala HA, Cao H, Secrest P, Friedmann-Morvinski D and others. 2011. Human xeno-autoantibodies against a non-human sialic acid serve as novel serum biomarkers and immunotherapeutics in cancer. Cancer Res 71(9):3352-63.

Ries L A. 1994. Influence of extent of disease, histology, and demographic factors on lung cancer survival in the SEER population-based data. Semin Surg Oncol 10(1):21-30.

Sanders R W, Venturi M, Schiffner L, Kalyanaraman R, Katinger H, Lloyd K O, Kwong P D, Moore J P. 2002. The mannose-dependent epitope for neutralizing antibody 2G12 on human immunodeficiency virus type 1 glycoprotein gp120. J Virol 76(14):7293-305.

Scanlan C N, Pantophlet R, Wormald M R, Ollmann Saphire E, Stanfield R, Wilson I A, Katinger H, Dwek R A, Rudd P M, Burton D R. 2002. The broadly neutralizing anti-human immunodeficiency virus type 1 antibody 2G12 recognizes a cluster of alpha1→2 mannose residues on the outer face of gp120. J Virol 76(14):7306-21.

Stamey T A, Caldwell M, McNeal J E, Nolley R, Hemenez M, Downs J. 2004. The prostate specific antigen era in the United States is over for prostate cancer: what happened in the last 20 years? J Urol 172(4 Pt 1):1297-301.

Stamey T A, Freiha F S, McNeal J E, Redwine E A, Whittemore A S, Schmid H P. 1993. Localized prostate cancer. Relationship of tumor volume to clinical significance for treatment of prostate cancer. Cancer 71(3 Suppl):933-8.

Stamey T A, McNeal J E, Yemoto C M, Sigal B M, Johnstone I M. 1999. Biological determinants of cancer progression in men with prostate cancer. Jama 281(15): 1395-400.

Trkola A, Purtscher M, Muster T, Ballaun C, Buchacher A, Sullivan N, Srinivasan K, Sodroski J, Moore J P, Katinger H. 1996. Human monoclonal antibody 2G12 defines a distinctive neutralization epitope on the gp 120 glycoprotein of human immunodeficiency virus type 1. J Virol 70(2): 1100-8.

Wandall H H, Blixt O, Tarp M A, Pedersen J W, Bennett E P, Mandel U, Ragupathi G, Livingston P O, Hollingsworth M A, Taylor-Papadimitriou J and others. 2010. Cancer biomarkers defined by autoantibody signatures to aberrant O-glycopeptide epitopes. Cancer Res 70(4):1306-13.

Wang D. 2012. N-glycan cryptic antigens as active immunological targets in prostate cancer patients. Journal Proteomics Bioinform 5:090-095.

Wang D, Herzenberg L A. 2011. Glycan markers and auto-antibody signatures in HIV-1 and HIV-1-associated malignancies. Patent application No. 20110177090, Files Jan 19, 2011. Assignee: The Board of Trustees of the Leland Stanford Junior University, Palo Alto, Calif.

Wang D, Herzenberg L A, Peehl D, Herzenberg L A. 2011. Prostate cancer glycan markers and auto-antibody signatures. U.S. Pat. No. 7,981,625. Jul. 19, 2011. Assigned to The Board of Trustees of the Leland Stanford Junior University, Palo Alto, Calif. (US).

Wang D, Liu S, Trummer B J, Deng C, Wang A. 2002. Carbohydrate microarrays for the recognition of cross-reactive molecular markers of microbes and host cells. Nat Biotechnol 20(3):275-81.

Wang L X. 2006. Toward oligosaccharide- and glycopeptide-based HIV vaccines. Curr Opin Drug Discov Devel 9(2):194-206.

Wang L X, Ni J, Singh S, Li H. 2004. Binding of high-mannose-type oligosaccharides and synthetic oligomannose clusters to human antibody 2G12: implications for HIV-1 vaccine design. Chem Biol 11(1):127-34.

Willyard C. 2010. Tiny steps towards an HIV vaccine. Nature 466(7304):58.

Example 2

N-glycan Cryptic Antigens as Active Immunological Targets in Prostate Cancer Patients Although tumor-associated abnormal glycosylation has been recognized for decades, information regarding host recognition of the evolving tumor glycome remains elusive. We report here a carbohydrate microarray analysis of a number of tumor-associated carbohydrates for their serum antibody reactivities and potential immunogenicity in humans. These are the precursors, cores and internal sequences of N-glycans, They are usually masked by other sugar moieties and belong to a class of glyco-antigens that are normally "cryptic". However, viral expression of these carbohydrates may trigger host immune responses. For examples, HIV-1 and SARS-CoV display Man9 clusters and tri- or multi-antennary type II (Galβ1β4GlcNAc) chains (Tri/m-II), respectively; viral neutralizing antibodies often target these sugar moieties. We asked, therefore, whether prostate tumor expression of corresponding carbohydrates triggers antibody responses in vivo. Using carbohydrate microarrays, we analyzed a panel of human sera, including 17 samples from prostate cancer patients and 12 from men with benign prostatic hyperplasia (BPH). We observed that IgG antibodies targeting the Man9- or Tri-/m-II-autoantigens are readily detectable in the sera of men with BPH, as well as those with cancer Importantly, these antibody activities were selectively increased in prostate cancer patients. Thus, human immune systems actively recognize these N-glycan cryptic carbohydrates and produce targeting antibodies.

Abbreviations: OR: orosomucoid; ASOR: asialo-orosomucoid; AGOR: agalacto-orosomucoid; Tri/m-II: tri-antennary and multivalent type II chains; Tri/m-Gn: tri-antennary and multivalent GlcNAc cores; PHA-L: Phaseolus vulgaris-L lectin; SNA: Sambucus nigra I agglutinin; GNA: Galanthus nivalis lectin; PCa: prostate cancer; BPH: benign prostatic hyperplasia.

Introduction

Recognition of tumor-associated abnormal glycosylation has raised a great interest in the potential for carbohydrate-based cancer biomarkers. For prostate cancer (PCa), a number of tumor-associated aberrant carbohydrates have been identified and characterized, including the glyco-isoforms of PSA (1-3), sulfated glycolipid (4), and blood group antigens and precursors (5, 6). The latter represent a diverse panel of O-glycans. These include, but are not limited to, T antigen (7, 8), Tn, sialyl and globo-H (9); the branched and linear type II backbone regions (I and i antigens); the difucosylated Le$^y$ or the monofucosyl, or monosialyl compound of sialyl-Le$^x$, blood group H, and Le$^b$ (10); type I backbone-based sialyl-Le$^a$ (11); and sialyl-Le$^x$ in association with metastatic PCa (12).

While carbohydrate researchers are exploring the diversities of tumor glycome, other investigators have turned their attention to the immunological properties of tumor-associated carbohydrates. Wandall et al. developed an O-glycopeptide microarray to monitor human autoantibody responses to tumor antigens that they successfully used to detect cancer-associated IgG autoantibodies against different aberrant O-glycopeptide epitopes derived from MUC1 in sera from breast, ovarian, and prostate cancer patients (13). Last year Blixt et al reported that the presence and level of autoantibodies were significantly higher in the sera from cancer patients compared with sera from the control subjects, and a highly significant correlation with age was observed. High levels of a subset of autoantibodies to the core3MUC1 and STnMUC1 glycoforms (GlcNAcβ1-3GalNAc-MUC1 and NeuAcα2,6GalNAc-MUC1, respectively) were significantly associated with reduced incidence and increased time to metastasis. These results suggest that autoantibodies to aberrantly glycosylated MUC1 in early stage breast cancer are associated with a better prognosis (14).

Padler-Karavani et al. (15) found that human carcinomas can metabolically incorporate the dietary non-human sialic acid Neu5Gc. That monosaccharide differs from the human sialic acid N-acetylneuraminic acid (Neu5Ac) by one oxygen atom but is able to trigger a differential antibody response. Using a novel sialoglycan microarray presenting multiple Neu5Gc-glycans and control Neu5Ac-glycans, these investigators found that antibodies against Neu5Gcalpha2-6GalNAcα1-O-Ser/Thr (GcSTn) are more prominent in patients with carcinomas than in patients with other diseases. Thus, these xeno-autoantibodies and xeno-autoantigens are considered potential targets for diagnostic, prognostic, and therapeutic applications in human carcinomas.

Our laboratory has been investigating a class of cryptic glycan markers that are differentially expressed among different Gleason grades of PCa and metastatic tumors (16-18). These markers include high-mannose (Man9) clusters; tri-antennary type II or multivalent type II (Tri/m-II) chains; and the agalactosyl derivatives, Tri-/m-Gn (GlcNAc)-glycoepitopes. They share the N-glycan Man-cores but differ in the terminal sugar moieties. Unlike the fully glycosylated cellular N-glycans, which are often capped by Neu5Ac, these targets expose the internal sequences that are normally "cryptic" to the immune systems. However, some viral pathogens express these carbohydrates on the surfaces of their virions. For examples, the HIV-1 envelop glycoprotein gp120 are heavily coated with Man9 clusters (19, 20) and the spike protein of SARS-CoV expresses Tri/m-II moieties (21). Importantly, viral neutralizing antibodies often target these carbohydrates (19-23).

One of the open questions is whether host immune systems recognize and respond to the tumor-expressed N-glycan cryptic carbohydrates. Newsom-Davis and Wang et al. recently reported that a tumor cell-based vaccine elicited anti-Man9-cluster antibodies (24). In this experiment, Fas-ligand-transfected melanoma cells were used for animal immunization. Flow cytometry analysis revealed that a monoclonal antibody (mAb), TM10, established by this immunization strategy illustrates a unique binding profile. TM 10 does not bind to the cell surface of untransformed normal cells but strongly binds to a number of murine and human tumor cell lines, including those from melanoma, prostate, breast, and ovarian cancers. Our carbohydrate microarray analysis revealed that TM10 recognizes the oligomannosyl epitopes presented by two Man9 clusters, (Man9)n-keyhole limpet hemocyanin (KLH) and [(Man9)4]n-KLH (24), which were constructed to investigate the HIV-1 neutralizing epitopes recognized by a human mAb 2G12 (19, 20).

These findings promoted us to investigate whether human immune systems recognize and respond to these tumor-associated cryptic glyco-antigens. In the current study, we characterized a panel of sera from men with PCa and sera from men with BPH using carbohydrate microarrays. Our rationale was that if these tumor carbohydrates were immunogenic in vivo, cancer patients would be possible to mount antibody responses to corresponding targets. Detection of these antibodies in PCa subjects by carbohydrate microarrays would provide evidence to pin down the specific immunological targets. Results of this study are summarized in this report.

Materials and methods

Serum Specimens, Antigens and Antibodies

A panel of 29 banked human sera specimens for analysis in this study was kindly provided by Dr. Zeqi (Joe) Zhou, of Egenix, Inc. (Millbrook, N.Y.). Diagnosis of PCa (N=17) or BPH (N=12) was based on the results of prostate needle biopsy in a clinic. Surgical Gleason grade information is, however, not available for this cohort. The specimens were blinded before we conducted our analysis.

Cy3-conjugated anti-human IgG used for carbohydrate microarray assay was purchased from Sigma (St. Louis, Mo). Carbohydrate antigens, glycoconjugates and other antigen preparations applied in this study are listed in Table 2.

Carbohydrate Microarrays

The microarrays used comprised 32 distinct antigen preparations, including 16 potential autoantigens and 16 common environmental antigens. The latter were selected because they often detect significant anti-carbohydrate antibodies in human circulation and can provide control probes for monitoring the global antibody profiles in a given subject. Members of the N-glycan cryptic sugar moieties, including Man-cores, Tri-/m-Gn, and Tri/m-II, were presented by a panel of spotted carbohydrate antigens. These include native human glycoproteins OR, ASOR, and AGOR, as well as two synthetic high-mannose clusters, (Man9)n-KLH and [(Man9)4]n-KLH (25-28).

For microarray printing, polysaccharides and glycoproteins were dissolved in saline and lipids were prepared as liposomes as described (29-32). Antigen solutions or liposome suspensions were spotted onto nitrocellulose-coated FAST slides (Schleicher & Schuell) by a high-precision robot designed to produce cDNA microarrays (Cartesian Technologies' PixSys 5500C) Immediately before use, the printed microarray slides were washed in 1xPBS at room temperature (RT) for 5 min, and blocked with 1% BSA-PBS at RT for 30 min They were incubated with 50 μl of sera (1:25) at RT for 1 hour, washed, and then incubated with titrated secondary anti-human IgG antibodies coupled with Cy3 at RT for 30 min. The stained slides were then rinsed five times and air-dried at RT before being scanned. The ScanArray5000A Microarray Scanner (PerkinElmer Life Science) was used to scan the stained microarrays for fluorescent signals. Fluorescent intensity values for each array spot and its background were calculated using ScanArray Express software (PerkinElmer Life Science).

Microarray Data-processing and Statistical Analysis.

Carbohydrate array datasets for 29 microarray assays, including sera from 17 PCa patients and 12 BPH patients, were standardized and statistically analyzed using the JMP Genomics software package from SAS Institute (Cary, N.C.). The standardized antibody reactivity (IgG) were determined as microarray scores, which are the log2 transformed (median-background) values normalized by setting their interquartile ranges (IQR) to be identical. One-way ANOVA was performed to compare the results obtained among groups and/or subgroups. Student's t test was applied to calculate the significance of differences among comparative groups.

Results

The first step of this carbohydrate microarray analysis was to characterize the global antibody profiles of all subjects. These profiles were measured as the relative serum antibody reactivities (IgG scores) with a diverse panel of antigens spotted in the same carbohydrate microarray. Statistical analyses were followed to identify the glycan markers that detect significant levels of autoantibodies in human circulation and further to those that capture PCa-associated autoantibody signatures.

Although the sera from the BPH and PCa subjects illustrate general similarity in their global antibody profiles, antibody reactivities targeting Man9 clusters spiked in the PCa sera. We also demonstrated statistically significant detection of autoantibodies by this microarray assay.

We addressed whether a given autoantigen detected antibodies in human sera. One-way analysis was performed to examine the significance of the differences of IgG scores among pairs of antigens. For examples, we examined pairs of OR-AGOR, OR-ASOR, and AGOR-ASOR, respectively. OR, ASOR, and AGOR are identical in their protein component but differ in the glyco-epitopes they express. AGOR and ASOR display Tri/m-Gn and Tri/m-II, respectively; OR does not surface-display either of the two glyco-epitopes. Thus, their pair-wise comparison is sufficient for revealing the carbohydrate-specific binding signals. OR did not detect measurable antibodies. By contrast, its asialo form, ASOR (Tri/m-II) and agalato form, AGOR (Tri/m-Gn) captured highly significant amounts of IgG antibodies.

KLH, Man9(2G12), and Man9 (TM10) share the KLH carrier but differ in carbohydrate units. Man9(2G12) and Man9 (TM10) display Man9 in different cluster configurations. By comparing antibodies captured by these conjugates with those of the KLH control, it was determined that the two Man9 clusters detected highly significant amounts of IgG antibodies in both the PCa and BPH groups.

We examined whether a detected serum autoantibody differed significantly between the PCa and BPH groups in order to identify potential "signatures" of PCa. For this purpose, autoantibodies detected in the PCa group were compared to those detected in the BPH group. The two Man9 clusters detected significantly increased levels of autoantibodies in the PCa group. Man9 (TM10) appears to be more effective than Man9 (2G12) in capturing serum IgG.

AGOR and ASOR did not detect significantly different levels of IgG between the PCa and BPH groups. However, a wide distribution of IgGASOR scores among samples from PCa patients was observed with a significant proportion of samples producing elevated levels of IgGASOR.

The repertoire of human serum antibodies is broad and diverse (33). How to standardize microarray datasets so that antibody profiles of different subjects can be quantitatively measured and meaningfully compared was a technical challenge to this study. We introduced the concept of Relative Antibody Reactivity (RAR) to standardize the global antibody profiles. In this way, the antibody profiles in comparison are independent of the serum antibody concentration, which is often subjected to the influences by a subject's physiological or pathological status in having blood drawn in the clinic.

Our results reveal that the global patterns of antigen-specific antibodies are impressively similar across subjects in both BPH and PCa groups. However, spikes of autoantibody activities emerged against the background of the conserved global antibody profiles. Interestingly, a number of spikes were identified in the same antigen ID# locations in the PCa- and BPH- plots. These are antigen ID #10, #12 and #26, which are Man9(2G12), Man9 (TM10), and cardiolipin, respectively. Based on this observation, we infer that preexisting autoantibodies contribute to the enhanced antibody responses to tumor carbohydrates.

In the background of the RAR-standardized global antibody profiles, we further examined statistically meaningful detection of autoantibodies in human circulations. Our carbohydrate microarrays detected significant levels of anti-ASOR (IgG$^{ASOR}$) and anti-AGOR (IgG$^{AGOR}$) antibodies in sera from both BPH and PCa patients. Since OR, ASOR, and AGOR have identical protein components, the differential antibody activities associated with them reflects glycan-binding specificities. Corresponding cryptic moieties of OR were marked by other sugar moieties. Thus, IgG$^{ASOR}$ captured by ASOR is predominantly Tri/m-II-specific; IgG$^{AGOR}$ detected by AGOR reflects binding of Tri/m-Gn.

Detection of IgG$^{ASOR}$ in human circulations is of particularl interest since their targeting carbohydrates, Tri-/m-II, are characterized by having β(1,6)-branched type II chains. Hyper-expression of β(1,6)-branched type II chains, as determined by PHA-L staining, has been found in a number of human cancers (39). Tissue-expression of this marker was also confirmed in the majority of PCa (16, 17). We further noticed that a significant number of dots of IgG$^{ASOR}$ in the PCa group are located above the upper 95% confidence limit line of the BPH group. This indicates that while the group means between PCa and BPH did not differ significantly (P=0.14306), a subset of PCa patients produced significantly increased levels of IgG$^{ASOR}$ compared with the BPH group. The IgGASOR specificities were also found in SARS-CoV neutralization antibodies (21), providing a rationale for the use of SARS-CoV neutralizing antibodies to kill the Tri-/m-II-positive tumor cells.

The two Man9 clusters captured substantially increased levels of IgGs compared to those detected by their common KLH carrier molecule. [(Man9)4]n-KLH preserves well the HIV-1-specific Man9-glyco-epitopes recognized by 2G12. (Man9)n-KLH is poorly reactive with 2G12 but is highly reactive with the anti-tumor mAb TM10. Since IgG scores associated with Man9(TM10) are significantly higher than the IgG scores of Man9(2G12), IgGMan9 detected in human sera are dominated by TM10-like anti-Man9-cluster antibodies. Both Man9 (TM10) and Man9 (2G12) detected significantly increased amounts of IgG antibodies in sera from the PCa group compared to sera from the BPH group. The Man9(TM10) conjugate is the most effective one in capturing serum IgGs among all autoantigens examined in this microarray analysis. In the context of tumor cell-surface expression of the TM10-antigens (24) and intensive expression of oligomannoses in the higher Gleason grade cancers (16), IgGMan9 provide a useful serum biomarker.

In summary, we have found in this study that autoantibodies targeting the Man9- or Tri-/m-II-glyco-antigens are readily detectable in human sera and that these antibody reactivities were selectively increased in PCa subjects.

REFERENCES

1. Prakash S, Robbins P W. Glycotyping of prostate specific antigen. Glycobiology. 2000;10(2):173-6.
2. Peracaula R, Tabares G, Royle L, Harvey D J, Dwek R A, Rudd P M, et al. Altered glycosylation pattern allows the distinction between prostate-specific antigen (PSA) from normal and tumor origins. Glycobiology. 2003;13(6):457-70.
3. Ohyama C, Hosono M, Nitta K, Oh-eda M, Yoshikawa K, Habuchi T, et al. Carbohydrate structure and differential binding of prostate specific antigen to Maackia amurensis lectin between prostate cancer and benign prostate hypertrophy. Glycobiology. 2004;14(8):671-9.
4. Palma A S, Liu Y, Childs R A, Herbert C, Wang D, Chai W, et al. The human epithelial carcinoma antigen recognized by monoclonal antibody AE3 is expressed on a sulfoglycolipid in addition to neoplastic mucins. Biochem Biophys Res Commun. 2011;408(4):548-52.
5. Abel P D, Marsh C, Henderson D, Leathem A, Powell P H, Williams G. Detection of blood group antigens in frozen sections of prostatic epithelium. Br J Urol. 1987;59(5):430-5.
6. Satoh M, Fukushi Y, Kawamura S, Ohyama C, Saito S, Orikasa S, et al. Glycolipid expression in prostatic tissue and analysis of the antigen recognized by antiprostatic monoclonal antibody APG1. Urol Int. 1992;48(1):20-4.
7. Moriyama H, Nakano M, Igawa M, Nihira H. T antigen expression in benign hyperplasia and adenocarcinoma of the prostate. Urol Int. 1987;42(2):120-3.
8. Ghazizadeh M, Kagawa S, Izumi K, Kurokawa K. Immunohistochemical localization of T antigen-like substance in benign hyperplasia and adenocarcinoma of the prostate. J Urol. 1984;132(6):1127-30.
9. Zhang S, Zhang H S, Reuter V E, Slovin S F, Scher H I, Livingston P O. Expression of potential target antigens for immunotherapy on primary and metastatic prostate cancers. Clin Cancer Res. 1998;4(2):295-302.
10. Chandrasekaran E V, Xue J, Xia J, Chawda R, Piskorz C, Locke R D, et al. Analysis of the specificity of sialyltransferases toward mucin core 2, globo, and related structures. identification of the sialylation sequence and the effects of sulfate, fucose, methyl, and fluoro substituents of the carbohydrate chain in the biosynthesis of selectin and siglec ligands, and novel sialylation by cloned alpha2,3(O) sialyltransferase. Biochemistry. 2005;44(47):15619-35.
11. Abel P D, Cornell C, Buamah P K, Williams G. Assessment of serum CA 19.9 as a tumour marker in patients with carcinoma of the bladder and prostate. Br J Urol. 1987;59(5):427-9.
12. Jorgensen T, Berner A, Kaalhus O, Tveter K J, Danielsen H E, Bryne M. Up-regulation of the oligosaccharide sialyl LewisX: a new prognostic parameter in metastatic prostate cancer. Cancer Res. 1995;55(9):1817-9.
13. Wandall H H, Blixt O, Tarp M A, Pedersen J W, Bennett E P, Mandel U, et al. Cancer biomarkers defined by autoantibody signatures to aberrant O-glycopeptide epitopes. Cancer Res. 2010;70(4):1306-13.
14. Blixt O, Bueti D, Burford B, Allen D, Julien S, Hollingsworth M, et al. Autoantibodies to aberrantly glycosylated MUC1 in early stage breast cancer are associated with a better prognosis. Breast Cancer Res. 2011;13(2):R25.
15. Padler-Karavani V, Hurtado-Ziola N, Pu M, Yu H, Huang S, Muthana S, et al. Human xeno-autoantibodies against a non-human sialic acid serve as novel serum biomarkers and immunotherapeutics in cancer. Cancer Res. 2011;71(9):3352-63.
16. Wang D, Herzenberg L A, Peehl D, Herzenberg L A. Prostate cancer glycan markers and auto-antibody signatures. U.S. Pat. No. 7,981,625. Jul. 19, 2011. Assigned to The Board of Trustees of the Leland Stanford Junior University, Palo Alto, Calif. (US). 2011.
17. Lange T, Ullrich S, Muller I, Nentwich M F, Stuebke K, Feldhaus S, et al. Human Prostate Cancer in a Clinically Relevant Xenograft Mouse Model: Identification of beta(1,6)-branched Oligosaccharides as a Marker of Tumor Progression. Clin Cancer Res. 2012.
18. Handerson T, Pawelek J M. Beta1,6-branched oligosaccharides and coarse vesicles: a common, pervasive phenotype in melanoma and other human cancers. Cancer Res. 2003;63(17):5363-9.
19. Trkola A, Purtscher M, Muster T, Ballaun C, Buchacher A, Sullivan N, et al. Human monoclonal antibody 2G12 defines a distinctive neutralization epitope on the gp120 glycoprotein of human immunodeficiency virus type 1. J Virol. 1996;70(2):1100-8.
20. Scanlan C N, Pantophlet R, Wormald M R, Ollmann Saphire E, Stanfield R, Wilson I A, et al. The broadly neutralizing anti-human immunodeficiency virus type 1 antibody 2G12 recognizes a cluster of alpha1→2 mannose residues on the outer face of gp120. J Virol. 2002;76(14):7306-21.
21. Wang D, Lu J. Glycan arrays lead to the discovery of autoimmunogenic activity of SARS-CoV. Physiol Genomics. 2004;18(2):245-8.
22. Wang D, Herzenberg L A. Glycan markers and auto-antibody signatures in HIV-1 and HIV-1-associated malignancies. Patent application No. 20110177090, Files Jan 19, 2011. Assignee: The Board of Trustees of the Leland Stanford Junior University, Palo Alto, Calif. 2011.
23. Sanders R W, Venturi M, Schiffner L, Kalyanaraman R, Katinger H, Lloyd K O, et al. The mannose-dependent epitope for neutralizing antibody 2G12 on human immunodeficiency virus type 1 glycoprotein gp120. J Virol. 2002; 76(14):7293-305.
24. Newsom-Davis T E, Wang D, Steinman L, Chen P F, Wang L X, Simon A K, et al. Enhanced immune recognition of cryptic glycan markers in human tumors. Cancer Res. 2009;69(5):2018-25.
25. Wang L X, Ni J, Singh S, Li H. Binding of high-mannose-type oligosaccharides and synthetic oligomannose clusters to human antibody 2G12: implications for HIV-1 vaccine design. Chem Biol. 2004;11(1):127-34.
26. Wang L X. Toward oligosaccharide- and glycopeptide-based HIV vaccines. Curr Opin Drug Discov Devel. 2006;9(2):194-206.
27. Ni J, Song H, Wang Y, Stamatos N M, Wang L X. Toward a carbohydrate-based HIV-1 vaccine: synthesis and immunological studies of oligomannose-containing glycoconjugates. Bioconjug Chem. 2006;17(2):493-500.

28. Li H, Wang L X. Design and synthesis of a template-assembled oligomannose cluster as an epitope mimic for human HIV-neutralizing antibody 2G12. Org Biomol Chem. 2004;2(4):483-8.

29. Wang D, Herzenberg L A, Steinman L. A lipid-based microarray and methods of use thereof. PCT International application No. PCT/U.S. 2006/011544, filed Mar. 22, 2006, claiming benefit of U.S. Provisional Application No. 60/664,251, filed Mar. 20, 2005.

30. Wang D, Liu S, Trummer B J, Deng C, Wang A. Carbohydrate microarrays for the recognition of cross-reactive molecular markers of microbes and host cells. Nat Biotechnol. 2002;20(3):275-81.

31. Liu Y, Childs R A, Palma A S, Campanero-Rhodes M A, Stoll M S, Chai W, et al. Neoglycolipid-based oligosaccharide microarray system: preparation of NGLs and their noncovalent immobilization on nitrocellulose-coated glass slides for microarray analyses. Methods Mol Biol. 2012; 808:117-36.

32. Wang D. Carbohydrate antigen microarrays. Methods Mol Biol. 2012;808:241-9.

33. Wang D, Kabat E A. Antibodies, Specificity. In: Encyclopedia of Immunology, Edn. Second (ed. Delves & Roitt). 1998:148-54.

34. Wang D, Wells S M, Stall A M, Kabat E A. Reaction of germinal centers in the T-cell-independent response to the bacterial polysaccharide alpha(1→6)dextran. Proc Natl Acad Sci U S A. 1994;91(7):2502-6.

35. Wang D, Liao J, Mitra D, Akolkar P N, Gruezo F, Kabat E A. The repertoire of antibodies to a single antigenic determinant. Mol Immunol. 1991;28(12):1387-97.

36. Seidl K J, MacKenzie J D, Wang D, Kantor A B, Kabat E A, Herzenberg L A, et al. Recurrent identical rearrangement and repeated expression of identical heavy and light chains in single anti-phosphatidylcholine B cells. Ann N Y Acad Sci. 1997;815:484-8.

37. Seidl K J, MacKenzie J D, Wang D, Kantor A B, Kabat E A, Herzenberg L A, et al. Frequent occurrence of identical heavy and light chain Ig rearrangements. Int Immunol. 1997;9(5):689-702.

38. Smith K, Garman L, Wrammert J, Zheng N Y, Capra J D, Ahmed R, et al. Rapid generation of fully human monoclonal antibodies specific to a vaccinating antigen. Nat Protoc. 2009;4(3):372-84.

39. Lau K S, Dennis J W. N-Glycans in cancer progression. Glycobiology. 2008;18(10):750-60.

TABLE 2

Microarray dataset for prostate cancer and BPH subjects

| Antigens (Reagent name, preparation code, and concentrations used for microarray printing) | ID | Prostate cancer (n = 17) Mean | SD | BPH (n = 12) Mean | SD | t-Test* p values |
|---|---|---|---|---|---|---|
| AGOR DW38 0.5 mg/ml | 1 | 0.179 | 0.303 | 0.225 | 0.209 | 0.63338 |
| AGOR DW38 0.5 mg/ml 1:5 in saline | 2 | −0.240 | 0.152 | −0.177 | 0.135 | 0.25008 |
| ASOR DW37 0.5 mg/ml | 3 | 0.348 | 0.416 | 0.149 | 0.295 | 0.14306 |
| ASOR DW37 0.5 mg/ml 1:5 in saline | 4 | −0.222 | 0.175 | −0.186 | 0.125 | 0.52734 |
| OR (1) DW749 0.5 mg/ml | 5 | −0.281 | 0.158 | −0.184 | 0.142 | 0.09732 |
| OR (1) DW749 0.5 mg/ml 1:5 in saline | 6 | −0.303 | 0.147 | −0.234 | 0.123 | 0.17942 |
| [(Man9)4]n-KLH DW951 0.5 mg/ml | 7 | 1.478 | 0.963 | 0.441 | 0.264 | 0.00045 |
| [(Man9)4]n-KLH DW951 0.5 mg/ml 1:5 in saline | 8 | 0.174 | 0.462 | −0.127 | 0.119 | 0.01901 |
| (Man9)n-KLH DW950 0.5 mg/ml | 9 | 2.367 | 1.304 | 0.927 | 0.597 | 0.00053 |
| (Man9)n-KLH DW950 0.5 mg/ml 1:5 in saline | 10 | 0.561 | 0.701 | 0.047 | 0.290 | 0.01253 |
| Man5-9-RB DW949 0.5 mg/ml | 11 | 0.148 | 0.298 | −0.050 | 0.159 | 0.02902 |
| Man5-9-RB DW949 0.5 mg/ml 1:5 in saline | 12 | −0.180 | 0.207 | −0.172 | 0.096 | 0.88286 |
| PtC L70905012 2 mg/ml | 13 | −0.007 | 0.377 | −0.025 | 0.157 | 0.86165 |
| PtC L70905012 2 mg/ml 1:5 in saline | 14 | −0.224 | 0.082 | −0.179 | 0.081 | 0.15456 |
| Sulfatide/PtC L70905-8 0.2 mg/2 mg/ml | 15 | 0.067 | 0.285 | −0.065 | 0.109 | 0.09704 |
| Sulfatide/PtC L70905-8 0.2 mg/2 mg/ml 1:5 in saline | 16 | −0.193 | 0.174 | −0.199 | 0.111 | 0.91021 |
| Ceramide/PTC L70905-9 0.2 mg/2 mg/ml | 17 | −0.093 | 0.156 | −0.096 | 0.096 | 0.93757 |
| Ceramide/PTC L70905-9 0.2 mg/2 mg/ml 1:5 in saline | 18 | −0.227 | 0.098 | −0.192 | 0.110 | 0.38436 |
| Cerebrosides/PTC DW876 L70905-10 0.2 mg/2 mg/ml | 19 | −0.019 | 0.343 | −0.101 | 0.087 | 0.35987 |
| Cerebrosides/PTC DW876 L70905-10 0.2 mg/2 mg/ml 1:5 in saline | 20 | −0.268 | 0.103 | −0.182 | 0.101 | 0.03544 |
| Ganglioside/PtC DW866 L70905-4 0.2 mg/2 mg/ml | 21 | −0.009 | 0.253 | −0.068 | 0.115 | 0.40170 |
| Ganglioside/PtC DW866 L70905-4 0.2 mg/2 mg/ml 1:5 in Saline | 22 | −0.193 | 0.104 | −0.159 | 0.111 | 0.41449 |
| GM1/PtC L70905-3 0.02 mg/2 mg/ml | 23 | 0.087 | 0.285 | 0.036 | 0.207 | 0.58106 |
| GM1/PtC L70905-3 0.02 mg/2 mg/ml 1:5 in saline | 24 | −0.130 | 0.086 | −0.092 | 0.127 | 0.38154 |
| Cardiolipin/PTC L70905-2 0.4 mg/2 mg/ml | 25 | 1.517 | 1.448 | 1.226 | 0.812 | 0.49720 |
| Cardiolipin/PTC L70905-2 0.4 mg/2 mg/ml 1:5 in saline | 26 | 0.191 | 0.193 | 0.113 | 0.212 | 0.32013 |
| Cardiolipin/PTC L70905-1 0.1 mg/2 mg/ml | 27 | 0.694 | 0.654 | 0.590 | 0.406 | 0.60242 |
| Cardiolipin/PTC L70905-1 0.1 mg/2 mg/ml 1:5 in saline | 28 | 0.117 | 0.181 | 0.021 | 0.075 | 0.06218 |

TABLE 2-continued

Microarray dataset for prostate cancer and BPH subjects

| Antigens (Reagent name, preparation code, and concentrations used for microarray printing) | ID | Glycan array scores (IgG) | | | | t-Test* |
|---|---|---|---|---|---|---|
| | | Prostate cancer (n = 17) | | BPH (n = 12) | | |
| | | Mean | SD | Mean | SD | p values |
| Glucocerebroside/PtC DW871 L70905-7 0.2 mg/2 mg/ml | 29 | −0.079 | 0.148 | −0.122 | 0.089 | 0.34495 |
| Glucocerebroside/PtC DW871 L70905-7 0.2 mg/2 mg/ml 1:5 in saline | 30 | −0.203 | 0.119 | −0.197 | 0.105 | 0.87167 |
| KLH-SH DW952 0.5 mg/ml | 31 | 0.273 | 0.385 | 0.067 | 0.175 | 0.06388 |
| KLH-SH DW952 0.5 mg/ml 1:5 in saline | 32 | −0.251 | 0.144 | −0.154 | 0.107 | 0.04831 |
| Phytosphingosine/PtC DW870 L70905 0.2 mg/2 mg/ml | 33 | −0.162 | 0.164 | −0.165 | 0.102 | 0.95493 |
| Phytosphingosine/PtC DW870 L70905 0.2 mg/2 mg/ml 1:5 in saline | 34 | −0.218 | 0.107 | −0.242 | 0.146 | 0.63965 |
| D-erythro-Sphingosine/PtC DW867 L70905-5 0.2/2 mg/ml | 35 | 0.085 | 0.310 | 0.011 | 0.167 | 0.41267 |
| D-erythro-Sphingosine/PtC DW867 L70905-5 0.2/2 mg/ml 1:5 in saline | 36 | −0.150 | 0.130 | −0.166 | 0.115 | 0.73325 |
| DMPS/PtC L70905-11 0.2 mg/2 mg/ml | 37 | −0.040 | 0.212 | −0.035 | 0.142 | 0.94828 |
| DMPS/PtC L70905-11 0.2 mg/2 mg/ml 1:5 in saline | 38 | −0.232 | 0.079 | −0.181 | 0.108 | 0.17961 |
| Yeast phosphomannan B2448 DW 41 0.5 mg/ml | 39 | 5.183 | 3.864 | 3.820 | 2.606 | 0.26686 |
| Yeast phosphomannan B2448 DW 41 0.5 mg/ml 1:5 in saline | 40 | 1.381 | 1.075 | 1.001 | 1.012 | 0.34126 |
| Dextran N279 DW49 0.5 mg/ml | 41 | 3.976 | 3.419 | 6.866 | 9.622 | 0.33697 |
| Dextran N279 DW49 0.5 mg/ml 1:5 in saline | 42 | 2.594 | 2.302 | 4.497 | 6.248 | 0.33160 |
| Dextran B1299S DW51 0.5 mg/ml | 43 | 3.861 | 4.786 | 4.438 | 6.773 | 0.80249 |
| Dextran B1299S DW51 0.5 mg/ml 1:5 in saline | 44 | 0.979 | 1.672 | 1.535 | 2.820 | 0.54899 |
| Dextran B1355S DW50 0.5 mg/ml | 45 | 1.701 | 1.501 | 2.996 | 1.925 | 0.06560 |
| Dextran B1355S DW50 0.5 mg/ml 1:5 in saline | 46 | 0.438 | 0.699 | 1.242 | 0.874 | 0.01553 |
| Levan DW42 0.5 mg/ml | 47 | 0.892 | 1.607 | 1.703 | 1.374 | 0.15690 |
| Levan DW42 0.5 mg/ml 1:5 in saline | 48 | 0.024 | 0.514 | 0.576 | 0.631 | 0.02092 |
| E. coli. LPS 5014 DW934 0.5 mg/ml | 49 | 0.365 | 2.313 | 0.951 | 1.805 | 0.45090 |
| E. coli. LPS 5014 DW934 0.5 mg/ml 1:5 in saline | 50 | −0.246 | 0.317 | 0.048 | 0.478 | 0.07881 |
| E. coli. LPS 2630 DW933 0.5 mg/ml | 51 | 0.291 | 0.454 | 0.657 | 0.790 | 0.16729 |
| E. coli. LPS 2630 DW933 0.5 mg/ml 1:5 in saline | 52 | −0.094 | 0.278 | 0.142 | 0.379 | 0.08278 |
| E. coli. K1 DW34 0.5 mg/ml | 53 | 1.564 | 1.338 | 1.192 | 1.305 | 0.46161 |
| E. coli. K1 DW34 0.5 mg/ml 1:5 in saline | 54 | −0.060 | 0.331 | 0.095 | 0.795 | 0.53541 |
| E. coli. K100 DW36 0.5 mg/ml | 55 | 3.108 | 2.824 | 4.251 | 3.094 | 0.32087 |
| E. coli. K100 DW36 0.5 mg/ml 1:5 in saline | 56 | 0.741 | 1.239 | 1.225 | 1.041 | 0.26494 |
| E. coli. K92 DW92 0.5 mg/ml | 57 | 0.204 | 0.518 | 0.023 | 0.281 | 0.23883 |
| E. coli. K92 DW92 0.5 mg/ml 1:5 in saline | 58 | −0.280 | 0.156 | −0.211 | 0.111 | 0.17709 |
| S. dysenterine type I O-SP DW 765 0.5 mg/ml | 59 | 2.344 | 2.377 | 2.696 | 3.009 | 0.73871 |
| S. dysenterine type I O-SP DW 765 0.5 mg/ml 1:5 in saline | 60 | 1.205 | 2.152 | 1.012 | 1.927 | 0.80189 |
| S. typhi LPS7261 DW932 1:5 in saline | 61 | 3.594 | 4.810 | 3.021 | 2.709 | 0.68697 |
| S. Typhi LPS7261 DW932 0.5 mg/ml | 62 | 6.126 | 6.838 | 5.600 | 5.634 | 0.82255 |
| Bacto-Agar DW801 0.5 mg/ml | 63 | 6.045 | 3.046 | 6.076 | 4.727 | 0.98460 |
| Dye mix. (Cy3, Cy5, FITC-AV 1:100) | 64 | 16.944 | 8.538 | 14.220 | 8.295 | 0.39797 |

*Results with significant difference (t-test p < 0.05) between prostate cancer group and BPH group were highlighted with BOLD.

What is claimed is:

1. A method of determining whether a man with a prostate specific antigen (PSA) level of <10 ng/ml has prostate cancer with a Gleason grade 4 or 5, the method comprising:
   (a) contacting an array of ($Man_9GlcNAc_2Asn$)-BSA conjugates immobilized on a substrate with a blood sample from the man with the PSA level of <10 ng/ml, and detecting the presence of anti-$Man_9$ antibodies of the sample under conditions wherein the anti-$Man_9$ antibodies bind the $Man_9$ of the ($Man_9GlcNAc_2Asn$)-BSA conjugates, wherein $Man_9$ is nonamannose, GlcNac is N-acetyl-D-glucosamine, Asn is asparagine and BSA is bovine serum albumin; and
   (b) measuring resultant binding of the anti-$Man_9$ antibodies of the sample to the $Man_9$ of the conjugates to determine a level of anti-$Man_9$ antibodies in the sample,
   wherein the level of the anti-$Man_9$ antibodies of the sample indicates that the man with the PSA level of <10 ng/ml has prostate cancer with Gleason grade 4 or 5.

2. The method of claim 1 wherein the man has prostate hyperplasia.

3. The method of claim 1 wherein the man is post-prostatectomy.

4. The method of claim 1 wherein the array further comprises asialoorosomucoid (ASOR), galacto-orosomucoid (AGOR) or orosomucoid (OR) immobilized at distinct positions on the substrate.

5. The method of claim 1 wherein the array further comprises asialoorosomucoid (ASOR), galacto-orosomucoid (AGOR) and orosomucoid (OR) immobilized at distinct positions on the substrate.

6. The method of claim 1, wherein the substrate is an epoxy-coated glass slide and the array is a microarray.

7. The method of claim 1, wherein the substrate is a hydrophobic polystyrene coated plastic microplate.

8. The method of claim 1, wherein the conjugates are immobilized by coating the surface with $Man_9$-BSA at 20 µg/ml in 0.1 M Sodium Bicarbonate Buffer Solution, pH 9.6 and incubating at 37° C. for 2hrs.

* * * * *